United States Patent [19]
Brar et al.

[11] Patent Number: 4,776,202
[45] Date of Patent: Oct. 11, 1988

[54] APPARATUS AND METHODS FOR TESTING SURFACE PROPERTIES OF A MATERIAL

[75] Inventors: Amarjit S. Brar, Edina; Jagdish P. Sharma, Bloomington; Suryanarayana Kaja, Eden Prairie, all of Minn.

[73] Assignee: Magnetic Peripherals Inc., Minneapolis, Minn.

[21] Appl. No.: 96,185

[22] Filed: Sep. 11, 1987

[51] Int. Cl.⁴ .......................... G01N 3/30; G01N 3/48
[52] U.S. Cl. ........................................... 73/12; 73/92; 73/844
[58] Field of Search .............. 73/82, 12, 844, 866, 73/849, 852

[56] References Cited

U.S. PATENT DOCUMENTS

| | | | |
|---|---|---|---|
| 2,892,342 | 6/1959 | Goss et al. | 73/12 |
| 3,209,585 | 10/1965 | Wolstenholme et al. | 73/844 |
| 3,266,289 | 8/1966 | Stamy | 73/82 |
| 3,425,263 | 2/1969 | Elliot et al. | 73/12 |
| 3,453,862 | 7/1969 | Elliot et al. | 73/12 |
| 3,576,127 | 4/1971 | Weitzel et al. | 73/12 |
| 3,956,925 | 5/1976 | Smith | 73/81 |
| 4,257,341 | 3/1981 | Roberts | 113/7 R |
| 4,313,337 | 2/1982 | Myint | 73/12 |
| 4,416,144 | 11/1983 | Chen et al. | 73/12 |
| 4,531,400 | 7/1985 | Nevel | 73/82 |

Primary Examiner—Stewart J. Levy
Assistant Examiner—Robert P. Bell
Attorney, Agent, or Firm—J. A. Genovese; R. M. Angus

[57] ABSTRACT

An apparatus for testing the surface properties of a material is disclosed. The apparatus includes an indentor which is suspended above the surface of a sample and dropped onto the sample. Several testing methods are also disclosed. Surface toughness is measured by dropping the indentor from a variable height and inspecting the surface for failure. Thin film strength is tested by making several drops from various heights and inspecting the surface for flaking of the layer. In addition, damping capacity can be measured by comparing the kinetic energy of the resulting from the drop of the indentor to the strain energy measured by a probe on the opposing surface of the sample.

1 Claim, 2 Drawing Sheets

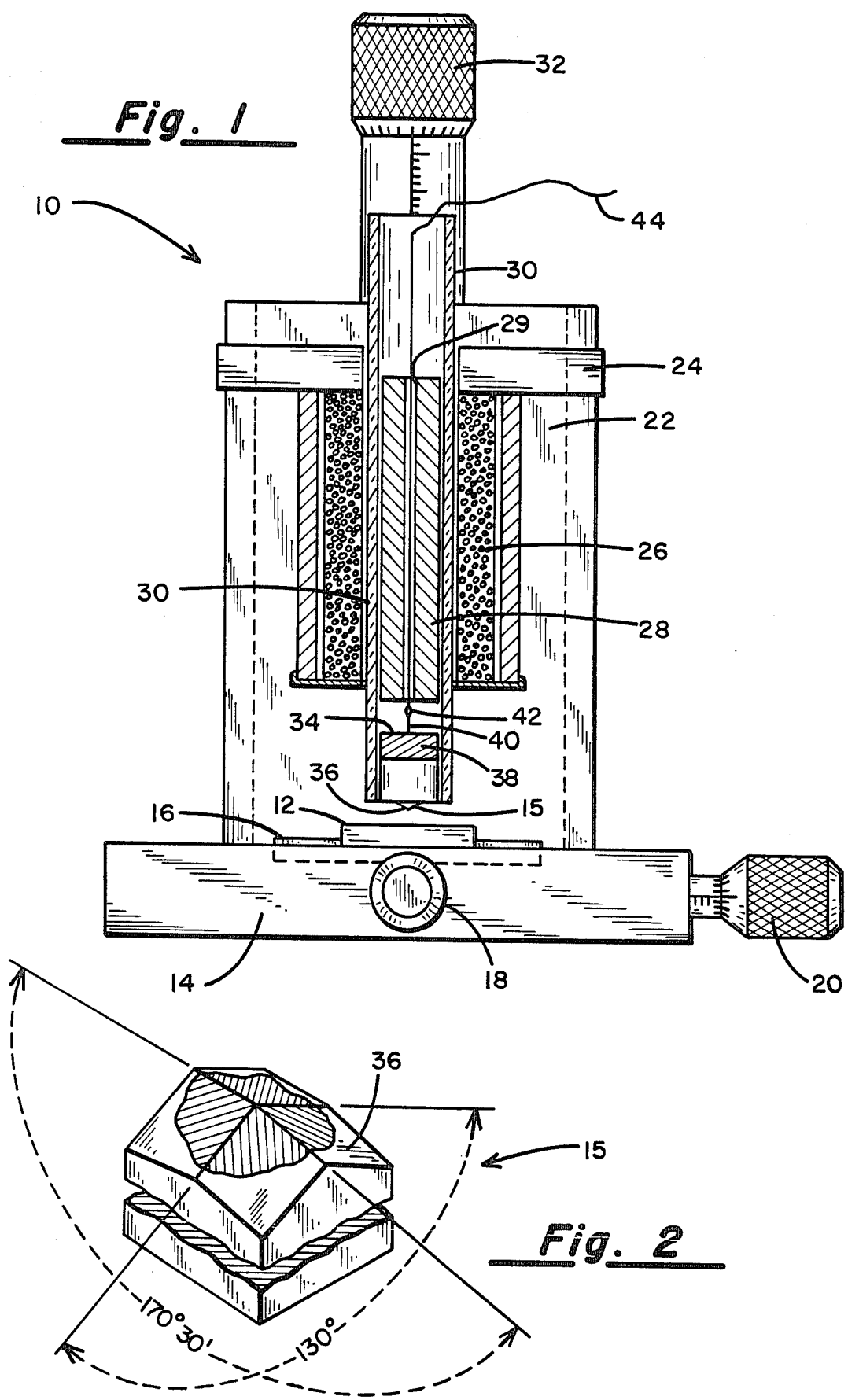

APPARATUS AND METHODS FOR TESTING SURFACE PROPERTIES OF A MATERIAL

BACKGROUND OF THE INVENTION

Many computers include at least one hard disk for data storage and a read/write head for writing data onto the hard disk or reading data from the disk. Small computers, such as personal computers, may have a hard disk and read/write head combination. Larger more powerful computers almost always are equipped with a number of these hard disks and read/write heads. There are also many data storage devices that use hard disks and read/write heads.

Generally as the computer operates the read/write heads fly over the hard disk. However, at times the read/write head contacts the disk, such as during take-off and landing of the read/write head.

An unintended contact between the head and the disk that results in a data loss is called a head crash. Head crashes result from a variety of reasons and are always undesirable in a data storage device.

Generally, data storage devices can operate for many hours before a head crash occurs. Head crashes can occur prematurely. The materials which make up the read/write head or hard disk are one possible cause for a premature head crash. The majority of the head is made from a ceramic material. The hard disk is a metal disk substrate with several thin layers of other materials which hold individual magnetic charges and lubricate the head to disk interface. If the ceramic material making up the head is too hard or brittle it can chip during takeoff or landing. If the bonding between the layers on the metal substrate is poor a layer may flake off when the head lands or takes off. In either case, the chip or flake could possibly lie on the disk and trip the read/write head on a subsequent rotation causing a head crash. One type of hard disk has a carbon overcoating. If the carbon overcoating is too soft it can accumulate on the head, eventually begin to drag and cause a premature head crash.

To date, the methods and apparatus used to test the materials making up the head and disk have been inadequate. Most test the bulk properties of a material rather than the surface properties. In addition, no tester seems to simulate the contact that occurs between the head and the disk during landing or takeoff.

As a result, there is a need for a tester capable of testing the surface properties of a material. Furthermore, there is a need for a tester and methods for using the tester that simulates the conditions that occur when the head and the disk contact during takeoff and landing.

SUMMARY OF THE INVENTION

A tester capable of testing the surface and composite thin film micro-properties of a material is disclosed, which is different than the measurement of bulk properties of materials. The tester is comprised of a sample holder, an indentor, and a mechanism for holding the indentor through a range of desired heights above a sample. The mechanism also releases the indentor so that kinetic energy is imparted upon the surface of the sample. Several testing methods including determination of the adhesion strength, the relative damping, capacity, micro-impact strength, micro-toughness, and surface deformation pattern at the surface are disclosed.

BRIEF DESCRIPTION OF THE DRAWINGS

For a better understanding of the present invention, reference may be had to the accompanying drawings in which:

FIG. 1 is a side view of the inventive tester.

FIG. 2 is a isometric view of a knoop indentor.

Figure 3:
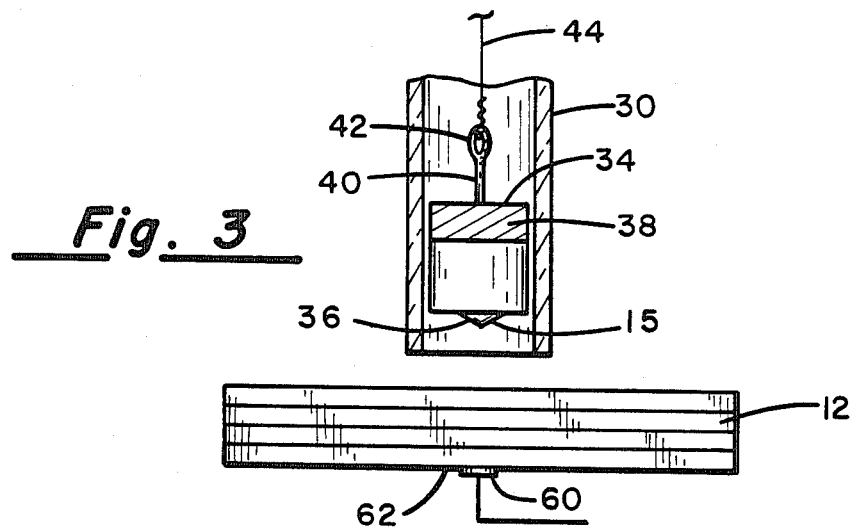
FIG. 3 is a view showing a cutaway of the hard disk and showing the arrangement for testing the damping capacity.

These drawings are not intended as a definition of the invention but are provided solely for the purpose of illustrating the preferred embodiment of the invention described below.

DETAILED DESCRIPTION OF THE INVENTION

An inventive tester 10 for testing the surface properties of a test specimen or sample 12 is shown in FIG. 1. The inventive tester 10 includes a base 14, an indentor 15 and means for suspending and guiding the indentor. The base 14 includes a table 16 which holds the sample 12. The table 16 is attached to a positioning means such as pair of micrometers 18 and 20. The micrometer 18 controls the position of the table 16 in a direction parallel with a first edge of the base 14. The micrometer 20 controls the position of the table 16 in a direction substantially perpendicular to the first edge of the base 14.

Attached to the base 14 is a back 22. A support arm 24 extends out from the back 22. Attached to the arm 24 is the means for suspending and guiding the indentor which includes a solenoid winding 26, a cylindrical core 28 and a guide 30. The core 28 includes an opening 29 which passes through its length. The opening 29 is also cylindrical in shape and the axis of the opening 29 and the core 28 are the same. The core 28 is positioned within the solenoid winding 26. The guide 30 is tubular and made of a nonmagnetic material such as glass or plastic. The guide 30 fits within the solenoid winding 26. The guide 30 is adjustable and can be extended beyond the end of the winding 26 toward the base 14.

The arm 24 is adjustably attached to the back 22. A micrometer 32 is used to move the arm 24 up and down the back 22 so that the indentor 15 can be dropped onto a sample 12 from a range of desired heights. In the preferred embodiment the drop height ranges from 0.0001" to 0.25". The drop heights are relatively small so that the indentor 15 makes indentations mainly in the surface of the sample 12.

The indentor 15 is basically cylindrical in shape and has a suspension end 34 and an indentor end 36. The suspension end 34 includes a cylindrical rod 38 made of a high magnetic permeability material. Centered in and extending out from the top of the rod 38 is a needle 40 having an opening 42 therein. A thread 44 is secured through the opening 42. The thread 44 also passes through the opening 29 in the core 28. The thread 44 is of ample length so that a portion extends out the end of the core 28 above the support arm 24.

The indentor end 36 can have a variety of shapes to assess the micro surface properties of materials. The knoop-indentor 25 shown in FIGS. 1 and 2 is essentially shaped like a pyramid having known dimensions. Generally, variety of indentors having the desired shaped ends for particular tests will be used rather than one indentor 15 with an interchangeable head. For example, it is contemplated that several indentors with different geometrical shaped ends having different heights will be used on samples having substantially different hardnesses. Another type of indentor 15 will have a ball-shaped indentor end 36. It should be noted that the indentor 15 may vary in weight. However, to conduct tests to determine the surface properties of a sample the indentor will generally weigh between 0.05 grams to 2 grams. The higher range may vary, of course, depending on the material being tested.

In operation the thread 44 is passed through the opening 29 in the core 28. The end of the thread is attached to the needle 40 through the opening 42 therein. The thread 44 is then pulled from the top to raise the indentor 15.

The indentor is lifted until the needle 40 on the suspension end 34 of the indentor 15 extends into the opening 29 of the core 28. At this point power is provided to the solenoid winding 26. This, as is well known in the art, induces a magnetic field which is concentrated in the core 28. The rod of high permeability material 38 on the indentor 15 is attracted to the core 28. The indentor 15 is held in place by the magnetic field produced.

The core 28 is made of a material which has high permeability and low coercivity. Thus when the power to the winding 26 is turned off, the core will have very little, if any, residual magnetism. The magnetic couple which suspended the indentor 15 disappears and allows the indentor 15 to fall substantially straight down. The guide 30 is generally moved into close proximity to the surface of the sample 12 to keep the indentor falling substantially straight down through each drop.

Before the indentor 15 is dropped, the sample 12 is placed below the indentor 15 on the table 16. Using the micrometers 18 and 20, the sample 12 can be precisely positioned at a desired location. Several testing methods require the sample to undergo more than one test. The micrometers 18 and 20 are then used to move the sample 12 so the indentor 15 falls on a new portion of the sample for the subsequent test.

The force or energy with which the indentor 15 strikes the surface can be varied by changing the height through which the indentor 15 falls. The height can be easily varied by using the micrometer 32. The micrometer 32 moves the support area 24 vertically which in turn varies the height of the suspension means attached thereto. The micrometer 32 also allows for slight height adjustments when only slight differences in the energy imparted on the surface are desired. The micrometer 32 also allows one to return to a particular height so as to substantially duplicate the energy imparted on the sample 12.

Types of Tests

Several testing methods and their uses are described in the following paragraphs. It should be noted that these tests are used to compare two materials which may come from different vendors or different batches. Consequently, some of the tests do not have specific units.

Damping Capacity Test

FIG. 3 shows the test setup necessary to conduct the damping capacity test. A damping probe 60 is placed in contact with the test specimen 12 at a location 62. The location 62 is on the opposite side of the test specimen 12 and directly below the point where the indentor 15 contacts the test specimen 12. The damping probe 60 is a transducer which measures the rate of change in the strain at the location 62.

The kinetic energy imparted on the surface of the test specimen 12 causes the material to contract and expand as it travels through the sample 12. It also causes the material at location 62 to expand and contract. The strain in the material, change in length per unit length, varies over time. The probe 60 measures the rate at which the strain of the material at location 62 changes over time. The rate at which the strain changes is directly related to the energy, known as the strain energy, in the material. The kinetic energy imparted by the indentor 15 can be calculated from the mass of the indentor and the height from which it is dropped. The kinetic energy imparted onto the sample 12 less the strain energy detected by the probe 60 yields the energy absorbed by the specimen 12. The energy absorbed by the specimen 12 determines the micro-damping and energy capacity of the specimen 12. The damping capacity test can be used for both the head material and the hard disk material.

Thin Film Adhesion Strength of a Disk

Figure 4:
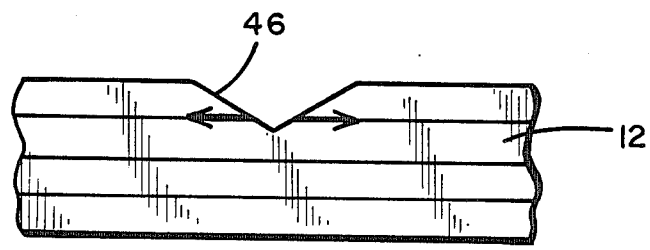
FIG. 4 is a side view of a multilayered sample. The arrows in FIG. 4 show the direction of forces and energy produced after the indentor is dropped onto the sample.

Now turning to FIG. 4, arrows show the direction in which a portion of the energy travels after the indentor strikes the surface of the sample 12. The arrows indicate that energy travels along the interfaces between the layers of the sample 12. The thin film adhesion strength test is a measure of the amount of energy the thin films can withstand before failing. The specimen 12 undergoes a series of drops by the indentor 15. The height of the indentor 15 is increased and the sample 12 is moved before each drop. The result is a series of tests sites or indentations of which have been subjected to different amounts of kinetic energy. An adhesive is applied to the surface of the sample 12 adjacent each test site. A lifting force is then applied to each test site to see if the thin layer of material adjacent the test site lifts off the test specimen 12. The test site with the maximum drop height of the indentor 15 in which the area adjacent the site does not lift off is the site of interest. Knowing the height through which the indentor 15 dropped and its weight, the maximum kinetic energy the thin layer of material can withstand is easily calculated. This test is used to compare the adhesion strength between the layers of a multilayered material. A typical use may be to compare the adhesion strength between two layers that were bonded by different processes.

Micro-Impact/Toughness Test For Any Surface

A specimen 12 is mounted to the table 16 of the tester 10. An indentor 15 of known geometry is raised to a prescribed height and dropped onto the surface of the specimen 12. The depth of penetration for the prescribed height indicates the micro-toughness of the material comprising the specimen 12.

A knoop type indentor 15, shown in FIGS. 1 and 2, has a known geometry from which the depth of penetration can be calculated. The length of the indentation is measured using a microscope. From the known geometry a ratio between the measured length and the depth of penetration is determined.

This test can be used to compare the micro-toughness of two materials. For example, after a first sample 12 undergoes a drop test, a sample 12 from a different vendor or from a different batch can then be mounted onto the tester 10. The indentor 15 is then dropped from the same height and the length of the indentation can be measured. The depth of penetration can then be determined and compared to the previous sample. The sample having the indentation of shorter length has a smaller depth of penetration and is therefore tougher.

Fracture Toughness Metalic Materials

The fracture toughness for a plastic material is the ability of a sample 12 to absorb energy and deform plastically. The sample is subjected to drops of the indentor 15 from various heights as the specimen 12 is moved between drops or tests. Preferably, the height is increased as the specimen is moved in one direction. This produces a line of test sites which have been subjected to an increasing amount of kinetic energy.

Figure 5:
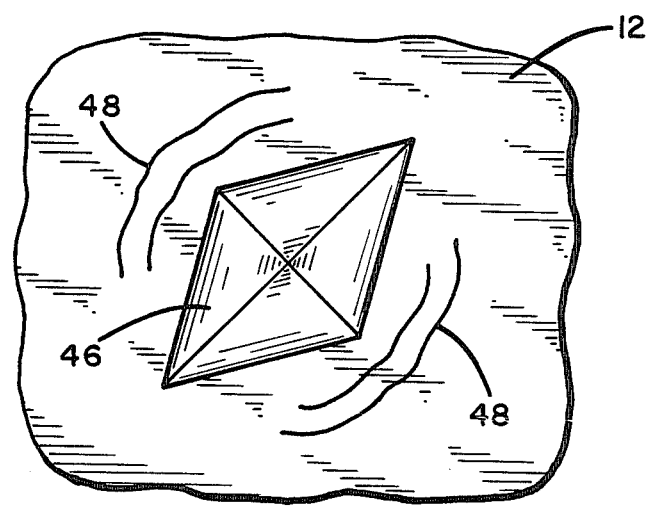
FIG. 5 is an enlarged view of an indentation in the surface of a sample.

The area adjacent the sites are then inspected using a microscope to look for evidence of deformation, pattern, shape and size. FIG. 5 shows an enlarged-view of the surface of a sample which has undergone plastic deformation. An indentation 46 is shown in the sample 12. Around the indentation 46 are ridges 48 which indicate plastic deformation of the surface.

The site having evidence of plastic deformation therewith indicates the amount of kinetic energy that can be absorbed at the surface of the sample 12 before deformation takes place as a measure of fracture toughness. This test is also used to indicate which of several samples has the highest tolerance toward kinetic energy or impact energy imparted at the surface.

Fracture Toughness Ceramics & Superconducting Materials

The same test procedure is followed when testing such material specimen 12 such as the ceramic head material. Once a series of test sites is produced with variable amounts of kinetic energy associated therewith, the specimen 12 is inspected using a microscope. The difference from the previous test is that the area adjacent the test sites are inspected for signs of chipping, and cracking rather than plastic deformation.

What we claim is:

1. A method for determining the micro damping capacity and energy capacity of a sample comprising the steps of:
    positioning the sample below an indentor;
    placing a strain energy detecting probe on the bottom of the sample, substantially directly below the indentor;
    dropping the indentor onto the sample from a predetermined drop distance above the sample as a function of the mass of the indentor and the predetermined drop distance;
    determining the amount of kinetic energy imparted on the surface of the sample;
    measuring the strain energy with the strain energy measuring probe; and
    determining the micro damping capacity and impact enery capacity of the sample by subtracting the strain energy measured by the probe from the kinetic energy imparted on the surface of the sample.

* * * * *